(12) United States Patent
Sakai (10) Patent No.: US 9,585,625 B2
(45) Date of Patent: Mar. 7, 2017

(54) RADIOGRAPHIC APPARATUS

(75) Inventor: Takihito Sakai, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1917 days.

(21) Appl. No.: 12/676,582

(22) PCT Filed: Sep. 25, 2007

(86) PCT No.: PCT/JP2007/068527
§ 371 (c)(1),
(2), (4) Date: Mar. 4, 2010

(87) PCT Pub. No.: WO2009/040880
PCT Pub. Date: Apr. 2, 2009

(65) Prior Publication Data
US 2010/0177949 A1    Jul. 15, 2010

(51) Int. Cl.
G06K 9/00 (2006.01)
A61B 6/00 (2006.01)
A61B 6/03 (2006.01)

(52) U.S. Cl.
CPC .............. *A61B 6/405* (2013.01); *A61B 6/032* (2013.01); *A61B 6/482* (2013.01)

(58) Field of Classification Search
USPC ................................................ 382/131, 132
See application file for complete search history.

(56) References Cited

U.S. PATENT DOCUMENTS

| 7,031,423 B2* | 4/2006 | Tsukagoshi | 378/4 |
| 7,599,541 B2* | 10/2009 | Hayashida | 382/132 |
| 7,822,169 B2* | 10/2010 | Roessl et al. | 378/5 |
| 2004/0101188 A1 | 5/2004 | Oosawa | |
| 2004/0156481 A1* | 8/2004 | Okamura et al. | 378/901 |
| 2004/0213377 A1 | 10/2004 | Endo | |
| 2005/0169427 A1* | 8/2005 | Halsmer et al. | 378/98.12 |
| 2006/0289774 A1* | 12/2006 | Endo et al. | 250/370.09 |
| 2008/0232668 A1* | 9/2008 | Kitamura et al. | 382/132 |

FOREIGN PATENT DOCUMENTS

| JP | 58-20089 A | 2/1983 |
| JP | 2000-232611 A | 8/2000 |
| JP | 2004-40422 A | 2/2004 |
| JP | 2004-186873 A | 7/2004 |
| JP | 2004-321310 A | 11/2004 |
| JP | 2007-21184 A | 2/2007 |

OTHER PUBLICATIONS

International Search Report for the Application No. PCT/JP2007/068527 mailed Dec. 25, 2007.

* cited by examiner

*Primary Examiner* — Neha Patel
(74) *Attorney, Agent, or Firm* — Cheng Law Group, PLLC (57) ABSTRACT

In the radiographic apparatus of this invention, a composite image generating device generates a composite high-voltage/low-voltage image for every time of the same high voltage/low voltage based on a plurality of high-voltage/low-voltage images successively acquired by a high-voltage/low-voltage image acquiring device. Based on the composite high-voltage/low-voltage image generated by the composite image generating device, a subtraction processing device carries out a subtraction process concerning high-voltage images and low-voltage images, to acquire subtraction images. Thus, a mistake by arithmetic processing is made inconspicuous without causing a dose shortage.

10 Claims, 4 Drawing Sheets

RADIOGRAPHIC APPARATUS

TECHNICAL FIELD

This invention relates to a radiographic apparatus that carries out radiographic imaging and, more particularly, relates to a technique of subtraction processes.

BACKGROUND ART

In radiographic imaging, a technique of energy subtraction is employed to select images of a soft part and images of a bony part. Subtraction images of a soft part or bony part can be outputted by acquiring high-voltage images and low-voltage images, and carrying out subtractions of these images. In recent years, a technique of carrying out energy subtraction in dynamic images has been proposed, in which radiation corresponding to a high voltage value and radiation corresponding to a low voltage value lower than that are emitted, as switched back and forth, to acquire high-voltage images and low-voltage images alternately, thereby acquiring subtraction images successively (see Patent Document 1, for example). In this technique of Patent Document 1, one of the high-voltage image and low-voltage image is acquired in the odd frames of (2m−1) frames, and the other of the high-voltage image and low-voltage image is acquired in even frames of 2m frames, to use an energy difference between the images in (2m−1) frames and 2m frames adjoining each other in time. And a subtraction process is carried out concerning the image in the (2m−1) frames and the image in the 2m frames.

Patent Document 1

Unexamined Patent Publication No. 2004-321310 (pages 1-6, 10-12, and FIG. 3)

DISCLOSURE OF THE INVENTION

Problem To Be Solved By The Invention

However, a mistake by arithmetic processing is sometimes noticeable when a subtraction process is simply carried out concerning images with time lags of a patient with motions. When radiographing rate is raised to reduce the time lags to a minimum in order to minimize such a mistake, energy emitted per unit time will become large correspondingly to the increase in radiographing rate, resulting in a shortage of dose for the low-voltage side.

This invention has been made having regard to the state of the art noted above, and its object is to provide a radiographic apparatus which makes a mistake by arithmetic processing inconspicuous without causing a shortage of dose.

Means For Solving The Problem

To fulfill the above object, this invention provides the following construction.

This invention provides a radiographic apparatus having a radiation emitting device for emitting radiation toward a patient, and a radiation detecting device for detecting radiation transmitted through the patient, to carry out radiation image pickup by obtaining radiographic images based on the detected radiation, the radiation emitting device being constructed to emit, as switched back and forth, radiation corresponding to a high voltage value and radiation corresponding to a low voltage value lower than that, the radiation detecting device being constructed to detect alternately the radiation corresponding to the high voltage value and the radiation corresponding to the low voltage value, and to output alternately radiation detection signals corresponding to the high voltage value and radiation detection signals corresponding to the low voltage value, the apparatus comprising a high-voltage image acquiring device for acquiring high-voltage images based on the radiation detection signals corresponding to the high voltage value detected, a low-voltage image acquiring device for acquiring low-voltage images based on the radiation detection signals corresponding to the low voltage value detected, a composite image generating device for generating a composite high-voltage image for every time of the same high voltage based on the plurality of high-voltage images successively acquired by the high-voltage image acquiring device, or generating a composite low-voltage image for every time of the same low voltage based on the plurality of low-voltage images successively acquired by the low-voltage image acquiring device, and a subtraction processing device for carrying out a subtraction process concerning the high-voltage images and the low-voltage images based on the composite high-voltage images or the composite low-voltage images generated by the composite image generating device, thereby to acquire subtraction images.

According to the radiographic apparatus of this invention, the radiation emitting device emits, as switched back and forth, radiation corresponding to a high voltage value and radiation corresponding to a low voltage value lower than that. The radiation detecting device alternately detects the radiation corresponding to the high voltage value and the radiation corresponding to the low voltage value noted above, and alternately outputs radiation detection signals corresponding to the high voltage value and radiation detection signals corresponding to the low voltage value. The high-voltage image acquiring device acquires high-voltage images based on the radiation detection signals corresponding to the high voltage value detected, and the low-voltage image acquiring device acquires low-voltage images based on the radiation detection signals corresponding to the low voltage value detected. Then, the composite image generating device generates a composite high-voltage image for every time of the same high voltage based on the plurality of high-voltage images successively acquired by the high-voltage image acquiring device, or generates a composite low-voltage image for every time of the same low voltage based on the plurality of low-voltage images successively acquired by the low-voltage image acquiring device. And the subtraction processing device carries out a subtraction process concerning the high-voltage images and the low-voltage images based on the composite high-voltage images or the composite low-voltage images generated by the composite image generating device, thereby to acquire subtraction images. Thus, even when the dose on the low voltage side is insufficient, the dose shortage can be compensated for by the composite image generating device generating composite (high-voltage/low-voltage) images based on the plurality of high-voltage images or low-voltage images. Since the composite (high-voltage/low-voltage) images are generated from the same high voltage or the same low voltage, a mistake in arithmetic processing caused by motion of the patient is averaged to render the mistake inconspicuous. As a result, the mistake by the arithmetic processing is made inconspicuous without causing a dose shortage.

In one example of the invention noted above, when in is a natural number, (A) the composite image generating device is arranged to generate a composite low-voltage image for 2m frame based on a low-voltage image of (2m−1) frame and a low-voltage image of (2m+1) frame acquired by the low-voltage image acquiring device, and the subtraction processing device is arranged to carry out a subtraction process concerning a high-voltage image of 2m frame acquired by the high-voltage image acquiring device and the composite low-voltage image of 2m frame generated by the composite image generating device, or (B) the composite image generating device is arranged to generate a composite low-voltage image for (2m+1) frame based on a low-voltage image of 2m frame and a low-voltage image of (2m+2) frame acquired by the low-voltage image acquiring device, and the subtraction processing device is arranged to carry out a subtraction process concerning a high-voltage image of (2m+1) frame acquired by the high-voltage image acquiring device and the composite low-voltage image of (2m+1) frame generated by the composite image generating device.

That is, when a low-voltage image is acquired in each odd frame, a composite low-voltage image is generated based on the low-voltage image of (2m−1) frame and the low-voltage image of (2m+1) frame adjoining each other in time across the even frame of 2m frame, and this composite low-voltage image is regarded as the image of 2m frame interposed in between. And a subtraction process is carried out on the high-voltage image and the composite low-voltage image, both being of 2m frame. When a low-voltage image is acquired in each even frame, a composite low-voltage image is generated based on the low-voltage image of 2m frame and the low-voltage image of (2m+2) frame adjoining each other in time across the odd frame of (2m+1), and this composite low-voltage image is regarded as the image of (2m+1) frame interposed in between. And a subtraction process is carried out on the high-voltage image and the composite low-voltage image, both being of (2m+1) frame.

In this example, in (A) a subtraction image is obtained for each 2m frame, and thus a subtraction image is obtained for each even frame. In (B), a subtraction image is obtained for each (2m+1) frame, and thus a subtraction image is obtained for each odd frame.

In another example of the invention noted above, when m is a natural number, (C) the composite image generating device is arranged to generate a composite high-voltage image for 2m frame based on a high-voltage image of (2m−1) frame and a high-voltage image of (2m+1), frame acquired by the high-voltage image acquiring device, and the subtraction processing device is arranged to carry out a subtraction process concerning a low-voltage image of 2m frame acquired by the low-voltage image acquiring device and the composite high-voltage image of 2m frame generated by the composite image generating device, or (D) the composite image generating device is arranged to generate a composite high-voltage image for (2m+1) frame based on a high-voltage image of 2m frame and a high-voltage image of (2m+2) frame acquired by the high-voltage image acquiring device, and the subtraction processing device is arranged to carry out a subtraction process concerning a low-voltage image of (2m+1) frame acquired by the low-voltage image acquiring device and the composite high-voltage image of (2m+1) frame generated by the composite image generating device.

That is, when a high-voltage image is acquired in each odd frame, a composite high-voltage image is generated based on the high-voltage image of (2m−1) frame and the high-voltage image of (2m+1) frame adjoining each other in time across the even frame of 2m frame, and this composite high-voltage image is regarded as the image of 2m frame interposed in between. And a subtraction process is carried out on the low-voltage image and the composite high-voltage image, both being of 2m frame. When a high-voltage image is acquired in each even frame, a composite high-voltage image is generated based on the high-voltage image of 2m frame and the high-voltage image of (2m+2) frame adjoining each other in time across the odd frame of (2m+1), and this composite high-voltage image is regarded as the image of (2m+1) frame interposed in between. And a subtraction process is carried out on the low-voltage image and the composite high-voltage image, both being of (2m+1) frame.

In this example, in (C) a subtraction image is obtained for each 2m frame, and thus a subtraction image is obtained for each even frame. In (D) a subtraction image is obtained for each (2m+1) frame, and thus a subtraction image is obtained for each odd frame.

In yet another example of the invention noted above, when m is a natural number, (E) the composite image generating device is arranged to generate a composite is high-voltage image for 2m frame based on a high-voltage image of (2m−1) frame and a high-voltage image of (2m+1) frame acquired by the high-voltage image acquiring device, while the composite image generating device is arranged to generate a composite low-voltage image for (2m+1) frame based on a low-voltage image of 2m frame and a low-voltage image of (2m+2) frame acquired by the low-voltage image acquiring device, and the subtraction processing device is arranged to carry out a subtraction process concerning a low-voltage image of 2m frame acquired by the low-voltage image acquiring device and the composite high-voltage image of 2m frame generated by the composite image generating device, while the subtraction processing device is arranged to carry out a subtraction process concerning a high-voltage image of (2m+1) frame acquired by the high-voltage image acquiring device and the composite low-voltage image of (2m+1) frame generated by the composite image generating device, or (F) the composite image generating device is arranged to generate a composite low-voltage image for 2m frame based on a low-voltage image of (2m−1) frame and a low-voltage image of (2m+1) frame acquired by the low-voltage image acquiring device, while the composite image generating device is arranged to generate a composite high-voltage image for (2m+1) frame based on a high-voltage image of 2m frame and a high-voltage image of (2m+2) frame acquired by the high-voltage image acquiring device, and the subtraction processing device is arranged to carry out a subtraction process concerning a high-voltage image of 2m frame acquired by the high-voltage image acquiring device and the composite low-voltage image of 2m frame generated by the composite image generating device, while the subtraction processing device is arranged to carry out a subtraction process concerning a low-voltage image of (2m+1) frame acquired by the low-voltage image acquiring device and the composite high-voltage image of (2m+1) frame generated by the composite image generating device.

That is, when a high-voltage image is acquired in each odd frame and a low-voltage image is acquired in each even frame, a composite high-voltage image is generated based on the high-voltage image of (2m−1) frame and the high-voltage image of (2m+1) frame adjoining each other in time across the even frame of 2m frame, and this composite high-voltage image is regarded as the image of 2m frame interposed in between, while a composite low-voltage image is generated based on the low-voltage image of 2m frame and the low-voltage image of (2m+2) frame adjoining each other in time across the odd frame of (2m+1) frame, and this composite low-voltage image is regarded as the image of (2m+1) frame interposed in between. And a subtraction process is carried out on the low-voltage image and the composite high-voltage image, both being of 2m frame, while a subtraction process is carried out on the high-voltage image and the composite low-voltage image, both being of (2m+1) frame. When a low-voltage image is acquired in each odd frame and a high-voltage image is acquired in each even frame, a composite low-voltage image is generated based on the low-voltage image of (2m−1) frame and the low-voltage image of (2m+1) frame adjoining each other in time across the even frame of 2m, and this composite low-voltage image is regarded as the image of 2m frame interposed in between, while a composite high-voltage image is generated based on the high-voltage image of 2m frame and the high-voltage image of (2m+2) frame adjoining each other in time across the odd frame of (2m+1), and this composite high-voltage image is regarded as the image of (2m+1) frame interposed in between. And a subtraction process is carried out on the high-voltage image and the composite low-voltage image, both being of 2m frame, while a subtraction process is carried out on the low-voltage image and the composite high-voltage image, both being of (2m+1) frame.

In this example, in any one of (E) and (F) a subtraction image is obtained for each of 2m frames and (2m+1) frames, and thus a subtraction image is obtained for each frame.

One example of composite (high-voltage/low-voltage) image generation is as follows. The composite image generating device is arranged to generate the composite high-voltage image by adding a plurality of high-voltage images successively acquired by the high-voltage image acquiring device, or to generate the composite low-voltage image by adding a plurality of low-voltage images successively acquired by the low-voltage image acquiring device.

Specifically, the composite high-voltage image for 2m frame is generated by adding a high-voltage image of (2m−1) frame and a high-voltage image of (2m+1) frame, or the composite high-voltage image for (2m+1) frame is generated by adding a high-voltage image of 2m frame and a high-voltage image of (2m+2) frame. Or the composite low-voltage image for 2m frame is generated by adding a low-voltage image of (2m−1) frame and a low-voltage image of (2m+1) frame, or the composite low-voltage image for (2m+1) frame is generated by adding a low-voltage image of 2m frame and a low-voltage image of (2m+2) frame.

Another example of composite (high-voltage/low-voltage) image generation is as follows. The composite image generating device is arranged to generate the composite high-voltage image by additive average (i.e. arithmetic average) in which a plurality of high-voltage images successively acquired by the high-voltage image acquiring device are added and the result is divided by the number of high-voltage images added, or to generate the composite low-voltage image by additive average (arithmetic average) in which a plurality of low-voltage images successively acquired by the low-voltage image acquiring device are added and the result is divided by the number of low-voltage images added.

Specifically, the composite high-voltage image for 2m frame is generated by additive average in which a high-voltage image of (2m−1) frame and a high-voltage image of (2m+1) frame are added, and the result is divided by 2 which is the number of high-voltage images added, or the composite high-voltage image for (2m+1) frame is generated by additive average in which a high-voltage image of 2m frame and a high-voltage image of (2m+2) frame are added, and the result is divided by 2 which is the number of high-voltage images added. Or the composite low-voltage image for 2m frame is generated by additive average in which a low-voltage image of (2m−1) frame and a low-voltage image of (2m+1) frame are added, and the result is divided by 2 which is the number of low-voltage images added, or the composite low-voltage image for (2m+1) frame is generated by additive average in which a low-voltage image of 2m frame and a low-voltage image of (2m+2) frame acquired by the low-voltage image acquiring device are added, and the result is divided by 2 which is the number of low-voltage images added.

Effects Of The Invention

According to the radiographic apparatus of this invention, a composite image generating device generates a composite high-voltage image for every time of the same high voltage based on a plurality of high voltage images successively acquired by a high-voltage image acquiring device, or generates a composite low-voltage image for every time of the same low voltage based on a plurality of low-voltage images successively acquired by a low-voltage image acquiring device. Based on the composite high-voltage image or composite low-voltage image generated by the composite image generating device, a subtraction processing device carries out a subtraction process concerning high-voltage images and low-voltage images, to acquire subtraction images. Thus, a mistake by arithmetic processing is made inconspicuous without causing a dose shortage.

DESCRIPTION OF REFERENCES

2 . . . X-ray tube
3 . . . flat panel X-ray detector (FPD)
9a . . . high- and low-voltage image acquiring unit
9b . . . composite image generating unit
9c . . . subtraction processing unit
M . . . patient Embodiment 1

Figure 1:
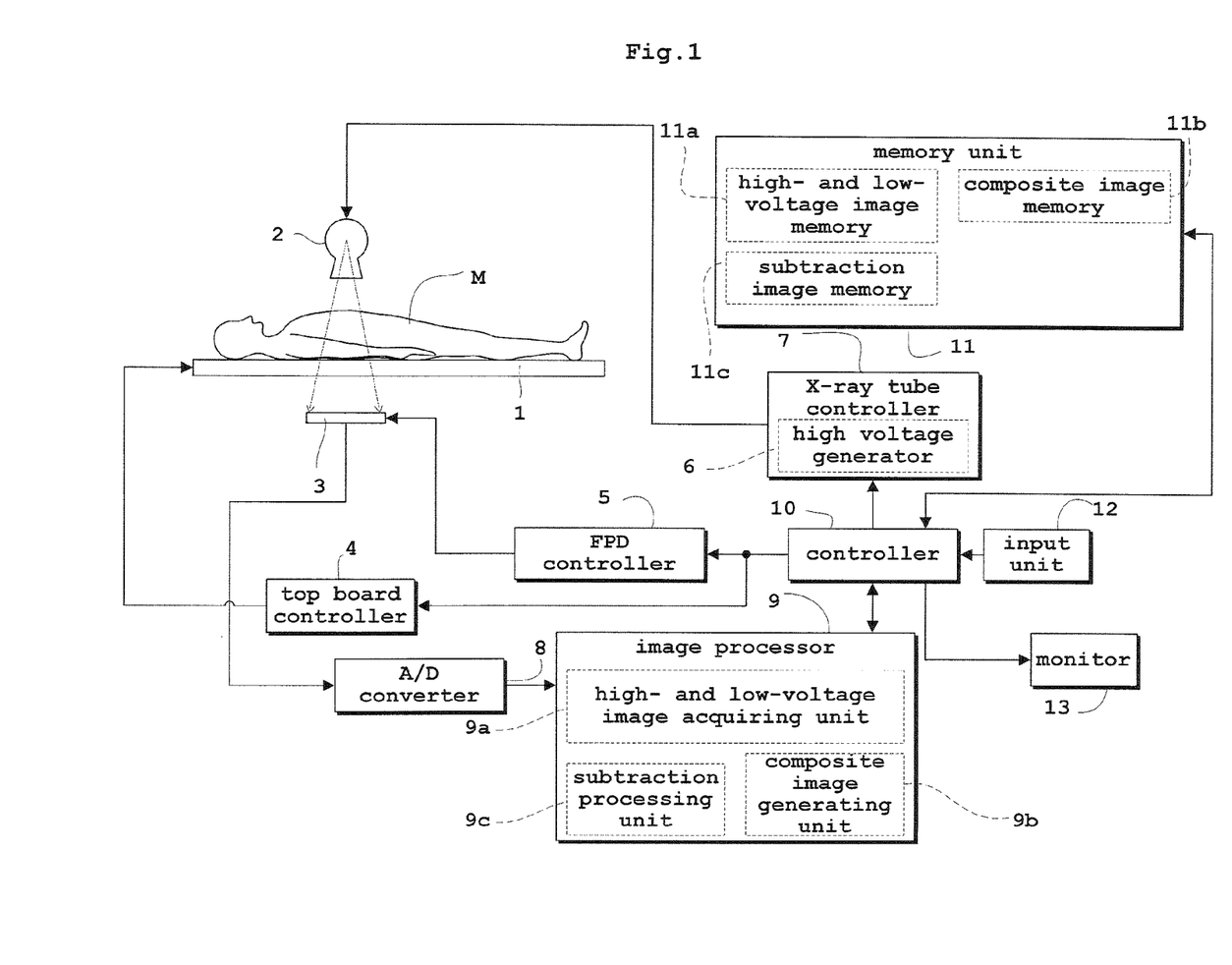
FIG. 1 is a block diagram of an X-ray imaging apparatus according to Embodiments 1-3.

Embodiment 1 of this invention will be described hereinafter with reference to the drawings. FIG. 1 is a block diagram of an X-ray imaging apparatus according to Embodiments 1-3. This Embodiment 1, including Embodiments 2 and 3 to follow, will be described, taking a flat panel X-ray detector (hereinafter abbreviated as "FPD") as an example of radiation detecting device, and the X-ray imaging apparatus as an example of radiographic apparatus.

As shown in FIG. 1, the X-ray imaging apparatus includes a top board 1 for supporting a patient M, an X-ray tube 2 for emitting X-rays toward the patient M, and an FPD 3 for detecting X-rays transmitted through the patient M. The X-ray tube 2 corresponds to the radiation emitting device in this invention. The FPD 3 corresponds to the radiation detecting device in this invention.

The X-ray imaging apparatus further includes a top board controller 4 for controlling vertical and horizontal movements of the top board 1, an FPD controller 5 for controlling scanning action of the FPD 3, an X-ray tube controller 7 having a high voltage generator 6 for generating tube voltages and tube currents for the X-ray tube 2, an analog-to-digital converter 8 for digitizing and fetching X-ray detection signals which are charge signals from the FPD 3, an image processor 9 for performing various processes based on the X-ray detection signals outputted from the analog-to-digital converter 8, a controller 10 for performing an overall control of these components, a memory unit 11 for storing processed images, an input unit 12 for the operator to input various settings, and a monitor 13 for displaying the processed images and other information.

The top board controller 4 controls movement of the top board 1, such as moving the top board 1 horizontally to place the patient M in an imaging position, vertically moving and/or rotating the top board 1 to set the patient M to a desired position, horizontally moving the top board 1 during an imaging operation, and horizontally moving the top board 1 to withdraw the patient M from the imaging position after the imaging operation. The FPD controller 5 performs controls relating to scanning by moving the FPD 3 horizontally and revolving it about the body axis of the patient M. The high voltage generator 6 generates the tube voltages and tube currents for application to the X-ray tube 2 to emit X-rays. The X-ray tube controller 7 performs controls relating to scanning by moving the X-ray tube 2 horizontally and revolving it about the body axis of the patient M, and controls also setting of an irradiation field of a collimator (not shown) adjacent the X-ray tube 2. In time of scanning with the X-ray tube 2 and FPD 3, the X-ray tube 2 and FPD 3 are movable, respectively, as opposed to each other so that the FPD 3 can detect X-rays emitted from the X-ray tube 2.

The controller 10 has a central processing unit (CPU) and other elements. The memory unit 11 has storage media, typically a ROM (Read-Only Memory) and RAM (Random Access Memory). The input unit 12 has a pointing device, typically a mouse, keyboard, joy stick, trackball and/or touch panel. The X-ray imaging apparatus picks up images of the patient M, with the FPD 3 detecting X-rays transmitted through the patient M, and the image processor 9 carrying out image processes based on the detected X-rays.

The image processor 9 includes a high- and low-voltage image acquiring unit 9a for acquiring high-voltage images and low-voltage images described hereinafter, a composite image generating unit 9b for generating a composite high-voltage image for each time of the same high voltage or a composite low-voltage image for each time of the same low voltage, and a subtraction processing unit 9c for carrying out subtraction processes concerning high-voltage images and low-voltage images based on the composite high-voltage image and composite low-voltage image to acquire subtraction images. The high- and low-voltage image acquiring unit 9a corresponds to the high-voltage image acquiring device and low-voltage image acquiring device in this invention. The composite image generating unit 9b corresponds to the composite image generating device in this invention. The subtraction processing unit 9c corresponds to the subtraction processing device. The high- and low-voltage image acquiring unit 9a acts as both the high-voltage image acquiring device and low-voltage image acquiring device in this invention. Specific functions of the high- and low-voltage image acquiring unit 9a, composite image generating unit 9b and subtraction processing unit 9c will be described hereinafter with reference to FIGS. 4 and 5.

The memory unit 11 is constructed to store, as written therein, each image processed by the image processor 9. Specifically, the memory unit 11 includes a high- and low-voltage image memory 11a for storing, as written therein, the high-voltage images and low-voltage images acquired by the high- and low-voltage image acquiring unit 9a, a composite image memory 11b for storing, as written therein, the composite high-voltage images and composite low-voltage images generated by the composite image generating unit 9b, and a subtraction image memory 11c for storing, as written therein, the images processed by the subtraction processing unit 9c as subtraction images. Specific functions of the high- and low-voltage image memory 11a, composite image memory 11b and subtraction image memory 11c will also be described hereinafter with reference to FIGS. 4 and 5.

Figure 2:
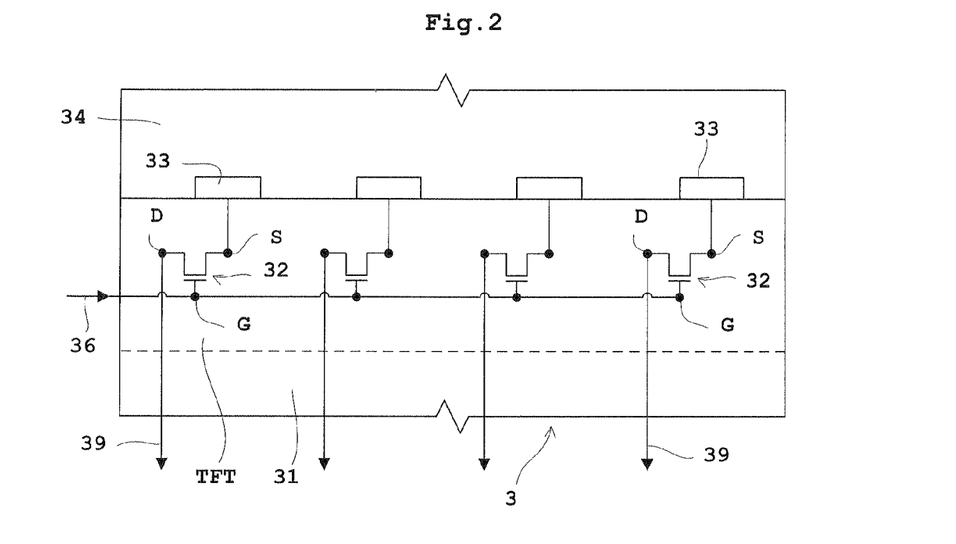
FIG. 2 is an equivalent circuit, seen in side view, of a flat panel X-ray detector (FPD)
Figure 3:
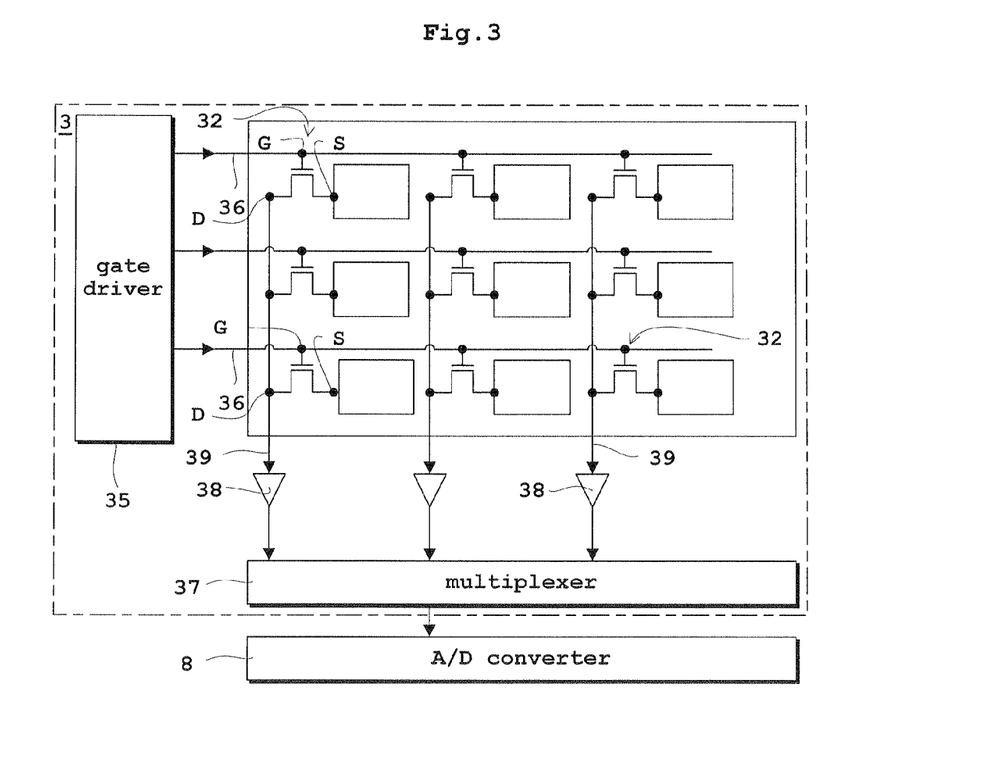
FIG. 3 is an equivalent circuit, seen in plan view, of the flat panel X-ray detector (FPD)

Next, the construction of the flat panel X-ray detector (FPD) 3 will be described with reference to FIGS. 2 and 3. FIG. 2 is an equivalent circuit, seen in side view, of the flat panel X-ray detector (FPD). FIG. 3 is an equivalent circuit, seen in plan view, of the flat panel X-ray detector (FPD).

As shown in FIG. 2, the FPD 3 includes a glass substrate 31, and thin film transistors TFT formed on the glass substrate 31. As shown in FIGS. 2 and 3, the thin film transistors TFT comprise numerous (e.g. 1,024×1,024) switching elements 32 arranged in a two-dimensional matrix of rows and columns. The switching elements 32 are formed separate from one another for respective carrier collecting electrodes 33. Thus, the FPD 3 is also a two-dimensional array radiation detector.

As shown in FIG. 2, an X-ray sensitive semiconductor 34 is laminated on the carrier collecting electrodes 33. As shown in FIGS. 2 and 3, the carrier collecting electrodes 33 are connected to the sources S of the switching elements 32. A plurality of gate bus lines 36 extend from a gate driver 35, and are connected to the gates G of the switching elements 32. On the other hand, as shown in FIG. 3, a plurality of data bus lines 39 are connected through amplifiers 38 to a multiplexer 37 for collecting charge signals and outputting as one. As shown in FIGS. 2 and 3, each data bus line 39 is connected to the drains D of the switching elements 32.

With a bias voltage applied to a common electrode not shown, the gates of the switching elements 32 are turned on by applying thereto (or reducing to 0V) the voltage of the gate bus lines 36. The carrier collecting electrodes 33 output charge signals (carriers) converted from X-rays incident on the detecting plane through the X-ray sensitive semiconductor 34, to the data bus lines 39 through the sources S and drains D of the switching elements 32. The charge signals are provisionally stored in capacitors (not shown) until the switching elements are turned on. The amplifiers 38 amplify the charge signals read out to the data bus lines 39, and the multiplexer 37 collects the charge signals, and outputs them as one charge signal. The analog-to-digital converter 8 digitizes the outputted charge signals, and outputs them as X-ray detection signals.

Figure 4:
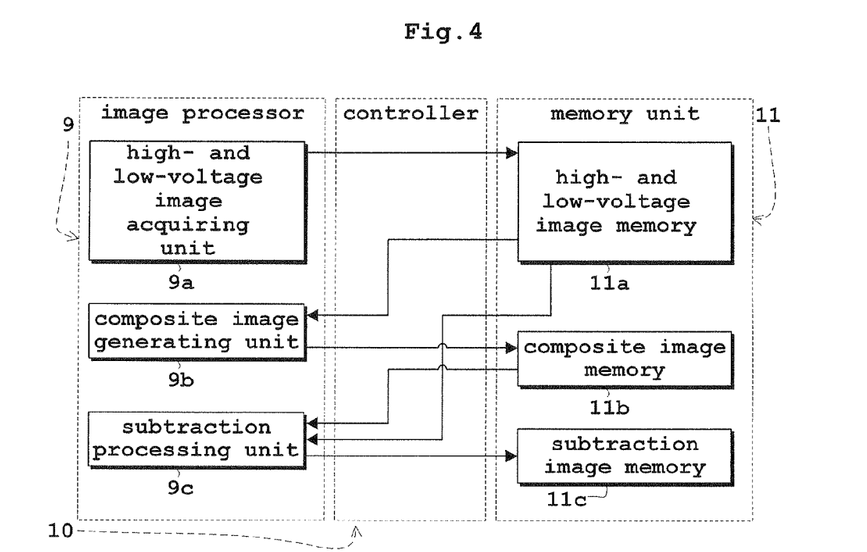
FIG. 4 is a schematic view showing data flows relating to an image processor and a memory unit.
Figure 5:
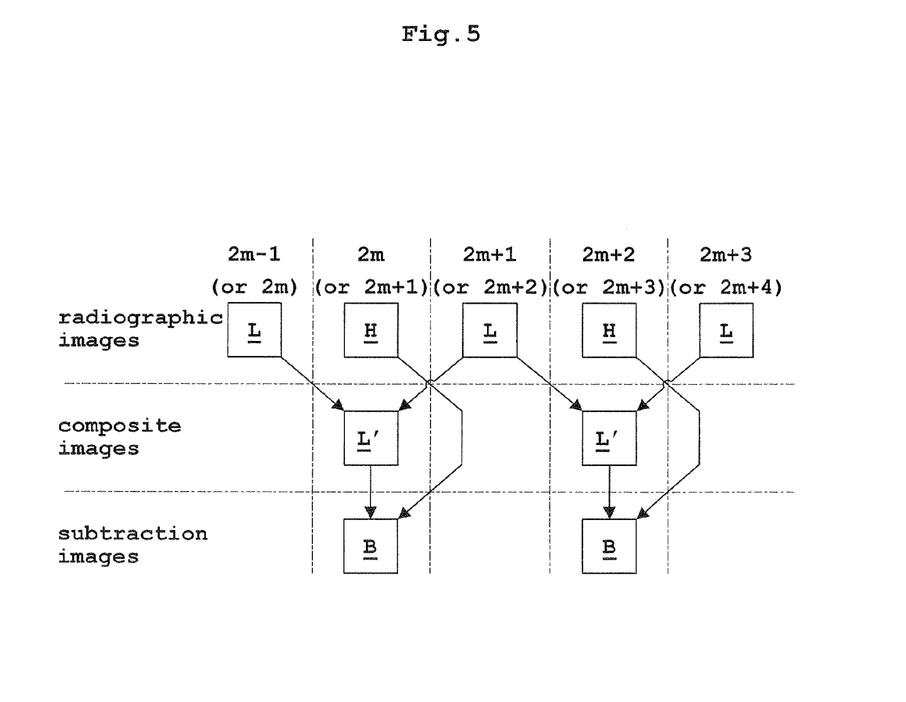
FIG. 5 is a schematic view showing data flows in Embodiment 1.

Next, specific functions of the high- and low-voltage image acquiring unit 9a, composite image generating unit 9b and subtraction processing unit 9c will be described with reference to FIGS. 4 and 5. FIG. 4 is a schematic view showing data flows relating to the image processor and memory unit. FIG. 5 is a schematic view showing data flows in Embodiment 1.

The high voltage generator 6 (see FIG. 1) applies, of the tube voltages, a high voltage (e.g. 120 kV) and a low voltage (e.g. 60 kV) lower than that to the X-ray tube 2 (see FIG. 1). The X-ray tube 2 emits, as switched back and forth, X-rays corresponding to the high voltage value and X-rays corresponding to the low voltage value noted above. When, for example, X-rays corresponding to the high voltage value are emitted for the first frame, X-rays corresponding to the low voltage value are emitted for the next, second frame. When emissions are made similarly hereinafter, as switched back and forth, X-rays corresponding to the high voltage value are emitted for odd frames of (2m−1), and X-rays corresponding to the low voltage value are emitted for even frames of 2m, where m is a natural number. Conversely, when X-rays corresponding to the low voltage value are emitted for the first frame, X-rays corresponding to the high voltage value are emitted for the next, second frame. When emissions are made similarly hereinafter, as switched back and forth, X-rays corresponding to the low voltage value are emitted for the odd frames of (2m−1), and X-rays corresponding to the high voltage value are emitted for the even frames of 2m. The FPD 3 (see FIGS. 1-3) alternately detects the X-rays corresponding to the high voltage value and the X-rays corresponding to the low voltage value, and alternately outputs X-ray detection signals corresponding to the high voltage value and X-ray detection signals corresponding to the low voltage value. The analog-to-digital converter S (see FIGS. 1 and 3) digitizes each X-ray detection signal.

As shown in FIG. 4, the X-ray high- and low-voltage image acquiring unit 9a acquires high-voltage images based on the X-ray detection signals corresponding to the high voltage value and low-voltage images based on the X-ray detection signals corresponding to the low voltage value, of the X-ray detection signals digitized by the analog-to-digital converter 8. Specifically pixel values are obtained as corresponding to signal values of the X-ray detection signals. Therefore, since signal values are higher for the X-ray detection signals corresponding to the high voltage value than for the X-ray detection signals corresponding to the low voltage, the pixel values of the high-voltage images acquired based on the X-ray detection signals corresponding to the high voltage value are higher than the pixel values of the low-voltage images acquired based on the X-ray detection signals corresponding to the low voltage value. The high-voltage images and low-voltage images acquired by the high- and low-voltage image acquiring unit 9a are written and stored in the high- and low-voltage image memory 11a.

When, as noted above, X-rays corresponding to the high voltage value are emitted for the odd frames of (2m−1), and X-rays corresponding to the low voltage value are emitted for the even frames of 2m, high-voltage images are acquired from the odd frames of (2m−1), respectively, and low-voltage images are acquired from 2m frames, respectively, which are stored in the high- and low-voltage image memory 11a. Conversely, when X-rays corresponding to the low voltage value are emitted for the odd frames of (2m−1), and X-rays corresponding to the high voltage value are emitted for the even frames of 2m, low-voltage images are acquired from the odd frames of (2m−1), respectively, and high-voltage images are acquired from 2m frames, respectively, which are stored in the high- and low-voltage image memory 11a.

The composite image generating unit 9b reads the high-voltage images and low-voltage images stored in the high- and low-voltage image memory 11a, respectively, and generates a composite high-voltage image for every time of the same high voltage based on a plurality of high-voltage images, or generates a composite low-voltage image for every time of the same low voltage based on a plurality of low-voltage images. As shown in FIG. 5, where H denotes high-voltage images, L denotes low-voltage images, L' denotes composite low-voltage images, and B denotes subtraction images, in this Embodiment 1, the composite image generating unit 9b generates a composite low-voltage image L' for every time of the same low voltage based on two low-voltage images L. In Embodiment 2 to follow, the composite image generating unit 9b generates a composite high-voltage image H' (see FIG. 6) for every time of the same high voltage based on two high-voltage images H. In Embodiment 3 to follow, the composite image generating unit 9b generates a composite high-voltage image H' (see FIG. 7) for every time of the same high voltage based on two high-voltage images H, and generates a composite low-voltage image L' for every time of the same low voltage based on two low-voltage images L.

In this Embodiment 1 in particular, as shown in FIG. 5, the composite image generating unit 9b generates a composite low-voltage image L' for 2m frame based on the low-voltage image L of (2m−1) frame and the low-voltage image L of (2m+1) frame. As a specific example of generation, the composite low-voltage image L' for 2m frame is generated by adding the low-voltage image L of (2m−1) frame and the low-voltage image L of (2m+1) frame. The composite low-voltage images L' for 2m frames generated by the composite image generating unit 9b are written and stored in the composite image memory 11b, respectively. In Embodiment 2 to follow, the composite high-voltage images H' generated by the composite image generating unit 9b are written and stored in the composite image memory 11b, respectively. In Embodiment 3 to follow, the composite high-voltage images H' and composite low-voltage images L' generated by the composite image generating unit 9b are written and stored in the composite image memory 11b, respectively.

The subtraction processing unit 9c reads the composite high-voltage images or composite low-voltage images stored in the composite image memory 11b, respectively, and carries out a subtraction process based on the composite high-voltage images or composite low-voltage images. In this Embodiment 1, as shown in FIG. 5, the subtraction processing unit 9c carries out a subtraction process based on the high-voltage images H stored in the high- and low-voltage image memory 11a and the composite low-voltage images L'. In Embodiment 2 to follow, the subtraction processing unit 9c carries out a subtraction process based on the low-voltage images L stored in the high- and low-voltage image memory 11a and the composite high-voltage images H'. In Embodiment 3 to follow, the subtraction processing unit 9c carries out a subtraction process based on the low-voltage images L stored in the high- and low-voltage image memory 11a and the composite high-voltage images H', and carries out a subtraction process based on the high-voltage images H stored in the high- and low-voltage image memory 11a and the composite low-voltage images L'.

In this Embodiment 1 in particular, as shown in FIG. 5, the subtraction processing unit 9c carries out a subtraction process concerning the high-voltage images H of 2m frames and the composite low-voltage images L' of 2m frames. A specific example of subtraction process is as follows.

Pixel value $X_R$ of a subtraction image is expressed by the following equation (1), where $X_H$ is a pixel value of high-voltage image H, $X_L$ is a pixel value of composite low-voltage image L', C is a difference coefficient used in the subtraction process, $N_1$ and $N_2$ are normalize coefficients used in the subtraction process, respectively, and $X_R$ is a pixel value of the subtraction image before dynamic range adjustment:

$$X_R = \{C \times \text{Log}(X_H/N_1) - \text{Log}(X_L/N_2)\} \quad (1)$$

$\text{Log}(X_H/N_1)$ in the above equation (1) is a logarithmic value obtained by dividing pixel value $X_H$ of high-voltage image H by normalize coefficient $N_1$. $\text{Log}(X_L/N_2)$ is a logarithmic value obtained by dividing pixel value $X_L$ of composite low-voltage image L' by normalize coefficient $N_2$.

Pixel value $X_R$ of the subtraction image derived from the above equation (1) is adjusted using a dynamic range. The pixel value of the subtraction image after adjustment is set to $X_L$, and scale S and offset O are set as the dynamic range. Pixel values $X_R$ and $X_L$ of the subtraction image before adjustment and after adjustment are expressed by the relationship as in the following equation (2):

$$X_L = X_R \times S + O \quad (2)$$

That is, the above equation (2) expresses pixel value $X_L$ of the subtraction image after adjustment in a linear function of pixel value $X_R$ of the subtraction image before adjustment where offset O is an intercept and the gradient is scale S. Thus, pixel value $X_R$ of the subtraction image derived from the foregoing equation (1) is adjusted with the above equation (2) to obtain pixel value $X_L$ of the subtraction image.

Images having the pixel value $X_L$ obtained in this way become subtraction images B as shown in FIG. 5. The subtraction images B processed by the subtraction processing unit 9c are written and stored in the subtraction image memory 11c, respectively. In Embodiment 2 to follow, the subtraction processing unit 9c carries out a subtraction process concerning the low-voltage images L and composite high-voltage images H', and the subtraction images B processed by the subtraction processing unit 9c are written and stored in the subtraction image memory 11c, respectively. In Embodiment 3 to follow, the subtraction processing unit 9c carries out a subtraction process concerning the low-voltage images L and composite high-voltage images H', the subtraction processing unit 9c carries out also a subtraction process concerning the high-voltage images H and composite low-voltage images L', and the subtraction images B processed by the subtraction processing unit 9c are written and stored in the subtraction image memory 11c, respectively.

To summarize the above, when X-rays corresponding to the low voltage value are emitted for the odd frame of (2m−1), and X-rays corresponding to the high voltage value are emitted for the even frame of 2m, in this Embodiment 1 the composite image generating unit 9b generates a composite low-voltage image L' for 2m frame based on low-voltage image L of (2m−1) frame and low-voltage image L of (2m+1) frame, and the subtraction processing unit 9c carries out a subtraction process concerning the high-voltage image H of 2m frame and the composite low-voltage image L' of 2m frame. Conversely, when X-rays corresponding to the high voltage value are emitted for the odd frame of (2m−1), and X-rays corresponding to the low voltage value are emitted for the even frame of 2m, in this Embodiment 1 the composite image generating unit 9b generates a composite low-voltage image L' for (2m+1) frame (see "(or 2m+1)" in FIG. 5) based on low-voltage image L of 2m frame (see "(or 2m)" in FIG. 5) and low-voltage image L of (2m+1) frame (see "(or 2m+1)" in FIG. 5), and the subtraction processing unit 9c carries out a subtraction process concerning the high-voltage image H of (2m+1) frame (see "(or 2m+1)" in FIG. 5) and the composite low-voltage image L' of (2m+1) frame (see "(or 2m+1)" in FIG. 5).

The frames are distinguished between odd number and even number as noted above because when the odd frames are high-voltage images, the even frames are low-voltage images, and when the odd frames are low-voltage images, the even frames are high-voltage images. The frames are distinguished between odd number and even number for generating composite (high-voltage/low-voltage) images, by using high-voltage images (or low-voltage images) of the odd frames, and using low-voltage images (or high-voltage images) of the even frames. In this Embodiment 1, the frames are distinguished between odd number and even number in order to carry out subtraction concerning high-voltage images and composite low-voltage images between the odd frames or even frames. Therefore, if the time of a starting frame changes, the frames will become either odd frames or even frames.

According to the X-ray imaging apparatus in this Embodiment 1, the X-ray tube 2 emits, as switched back and forth, X-rays corresponding to the high voltage value and X-rays corresponding to the low voltage value lower than that. The flat panel X-ray detector (FPD) 3 alternately detects the X-rays corresponding to the above high voltage value and the X-rays corresponding to the low voltage value, and alternately outputs X-ray detection signals corresponding to the high voltage value and X-ray detection signals corresponding to the low voltage value. The high- and low-voltage image acquiring unit 9a acquires high-voltage images based on the detected X-ray detection signals corresponding to the high voltage value, and low-voltage images based on the detected X-ray detection signals corresponding to the low voltage value.

Then, the composite image generating unit 9b generates a composite high-voltage image for every time of the same high voltage based on a plurality of high-voltage images successively acquired by the high- and low-voltage image acquiring unit 9a, or generates a composite low-voltage image for every time of the same low voltage based on a plurality of low-voltage images successively acquired by the high- and low-voltage image acquiring unit 9a. And the subtraction processing unit 9c acquires subtraction images by carrying out subtraction processes concerning the high-voltage images and the low-voltage images based on the composite high-voltage images or composite low-voltage images generated by the composite image generating unit 9b. Thus, even when the dose on the low voltage side is insufficient, the dose shortage can be compensated for by the composite image generating unit 9b generating composite (high-voltage/low-voltage) images based on a plurality of high-voltage images or low-voltage images. Since the composite (high-voltage/low-voltage) images are generated from the same high voltage or the same low voltage, a mistake in arithmetic processing caused by motion of the patient M is averaged to render the mistake inconspicuous. As a result, the mistake by the arithmetic processing is made inconspicuous without causing a dose shortage.

In this Embodiment 1, as shown in FIG. 5, the composite image generating unit 9b generates a composite low-voltage image L' for 2m frame based on the low-voltage image L of (2m−1) frame and the low-voltage image L of (2m+1) frame acquired by the high- and low-voltage image acquiring unit 9a. The subtraction processing unit 9c carries out a subtraction process concerning the high-voltage image H of 2m frame acquired by the high- and low-voltage image acquiring unit 9a and the composite low-voltage image L' of 2m frame generated by the composite image generating unit 9b. Or, the composite image generating unit 9b generates a composite low-voltage image L' for (2m+1) frame based on the low-voltage image L of 2m frame and the low-voltage image L of (2m+2) frame acquired by the high- and low-voltage image acquiring unit 9a. The subtraction processing unit 9c carries out a subtraction process concerning the high-voltage image H of (2m+1) frame acquired by the high- and low-voltage image acquiring unit 9a and the composite low-voltage image L' of (2m+1) frame generated by the composite image generating unit 9b.

That is, when low-voltage image L is acquired in each odd frame, a composite low-voltage image L' is generated based on low-voltage image L of (2m−1) frame and low-voltage image L of (2m+1) frame adjoining each other in time across the even frame of 2m, and this composite low-voltage image L' is regarded as the image of 2m frame interposed in between. And a subtraction process is carried out on high-voltage image H and composite low-voltage image L', both being of 2m frame. When low-voltage image L is acquired in each even frame, a composite low-voltage image L' is generated based on low-voltage image L of 2m frame and low-voltage image L of (2m+2) frame adjoining each other in time across the odd frame of (2m+1), and this composite low-voltage image L' is regarded as the image of (2m+1) frame interposed in between. And a subtraction process is carried out on high-voltage image H and composite low-voltage image L', both being of (2m+1) frame.

In this Embodiment 1, as shown in FIG. 5, subtraction image B is obtained for each 2m frame, and thus subtraction image B is obtained for each even frame. Subtraction image B is obtained for each (2m+1) frame (see "(or 2m+1)" in FIG. 5), and thus subtraction image B is obtained for each odd frame.

Embodiment 2

Figure 6:
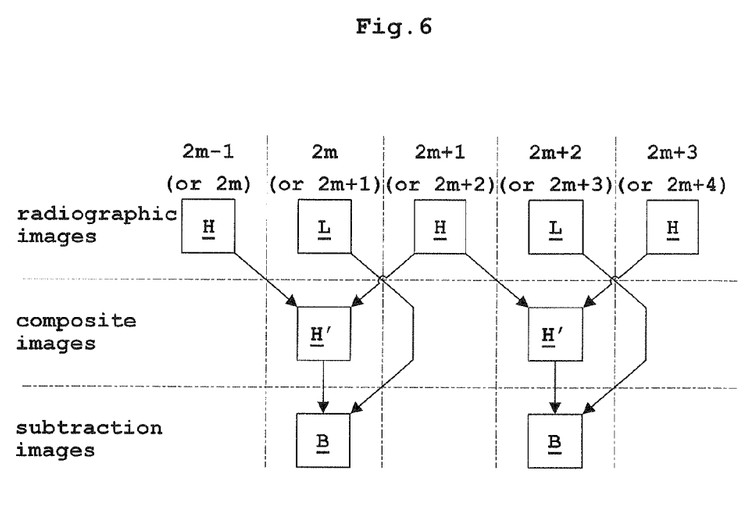
FIG. 6 is a schematic view showing data flows in Embodiment 2.

Next, Embodiment 2 of this invention will be described with reference to the drawings. FIG. 6 is a schematic view showing data flows in Embodiment 2.

As shown in FIG. 6, where H' denotes composite high-voltage images, in this Embodiment 2 the composite image generating unit 9b generates a composite high-voltage image H' for every time of the same high voltage based on two high-voltage images H. In this Embodiment 2 in particular, as shown in FIG. 6, the composite image generating unit 9b generates a composite high-voltage image H' for 2m frame based on the high-voltage image H of (2m−1) frame and the high-voltage image H of (2m+1) frame. As a specific example of generation, the composite high-voltage image H' for 2m frame is generated by adding the high-voltage image H of (2m−1) frame and the high-voltage image H of (2m+1) frame. The composite high-voltage images H' for 2m frames generated by the composite image generating unit 9b are written and stored in the composite image memory 11b, respectively.

The subtraction processing unit 9c carries out a subtraction process based on the low-voltage images L stored in the high- and low-voltage image memory 11a and the composite high-voltage images H'. That is, the subtraction processing unit 9c carries out a subtraction process concerning the low-voltage images L and composite high-voltage images H', and subtraction images B processed by the subtraction processing unit 9c are written and stored in the subtraction image memory 11c, respectively.

To summarize the above, when X-rays corresponding to the high voltage value are emitted for the odd frames of (2m−1), and X-rays corresponding to the low voltage value are emitted for the even frames of 2m, in this Embodiment 2 the composite image generating unit 9b generates a composite high-voltage image H' for 2m frame based on high-voltage image H of (2m−1) frame and high-voltage image H of (2m+1) frame, and the subtraction processing unit 9c carries out a subtraction process concerning the low-voltage image L of 2m frame and the composite high-voltage image H' of 2m frame. Conversely, when X-rays corresponding to the low voltage value are emitted for the odd frames of (2m−1), and X-rays corresponding to the high voltage value are emitted for the even frames of 2m, in this Embodiment 2 the composite image generating unit 9b generates a composite high-voltage image H' for (2m+1) frame (see "(or 2m+1)" in FIG. 6) based on high-voltage image H of 2m frame (see "(or 2m)" in FIG. 6) and high-voltage image H of (2m+2) frame (see "(or 2m+2)" in FIG. 6), and the subtraction processing unit 9c carries out a subtraction process concerning the low-voltage image L of (2m+1) frame (see "(or 2m+1)" in FIG. 6) and the composite high-voltage image H' of (2m+1) frame (see "(or 2m+1)" in FIG. 6).

According to the X-ray imaging apparatus in this Embodiment 2, as in Embodiment 1, the composite image generating unit 9b generates a composite high-voltage image for every time of the same high voltage based on a plurality of high-voltage images successively acquired by the high- and low-voltage image acquiring unit 9a, or generates a composite low-voltage image for every time of the same low voltage based on a plurality of low-voltage images successively acquired by the high- and low-voltage image acquiring unit 9a. The subtraction processing unit 9c acquires subtraction images by carrying out subtraction processes concerning the high-voltage images and the low-voltage images based on the composite high-voltage images or composite low-voltage images generated by the composite image generating unit 9b. Thus, a mistake by arithmetic processing is made inconspicuous without causing a dose shortage.

In this Embodiment 2, as shown in FIG. 6, the composite image generating unit 9b generates a composite high-voltage image H' for 2m frame based on the high-voltage image H of (2m−1) frame and the high-voltage image H of (2m+1) frame acquired by the high- and low-voltage image acquiring unit 9a. The subtraction processing unit 9c carries out a subtraction process concerning the low-voltage image L of 2m frame acquired by the high- and low-voltage image acquiring unit 9a and the composite high-voltage image H' of 2m frame generated by the composite image generating unit 9b. Or, the composite image generating unit 9b generates a composite high-voltage image H' for (2m+1) frame based on the high-voltage image H of 2m frame and the high-voltage image H of (2m+2) frame acquired by the high- and low-voltage image acquiring unit 9a. The subtraction processing unit 9c carries out a subtraction process concerning the low-voltage image L of (2m+1) frame acquired by the high- and low-voltage image acquiring unit 9a and the composite high-voltage image H' of (2m+1) frame generated by the composite image generating unit 9b.

That is, when high-voltage image H is acquired in each odd frame, a composite high-voltage image H' is generated based on high-voltage image H of (2m−1) frame and high-voltage image H of (2m+1) frame adjoining each other in time across the even frame of 2m frame, and this composite high-voltage image H' is regarded as the image of 2m frame interposed in between. And a subtraction process is carried out on low-voltage image L and composite high-voltage image H', both being of 2m frame. When high-voltage image H is acquired in each even frame, a composite high-voltage image H' is generated based on high-voltage image H of 2m frame and high-voltage image H of (2m+2) frame adjoining each other in time across the odd frame of (2m+1), and this composite high-voltage image H' is regarded as the image of (2m+1) frame interposed in between. And a subtraction process is carried out on low-voltage image L and composite high-voltage image H', both being of (2m+1) frame.

In this Embodiment 2, as shown in FIG. 6, subtraction image B is obtained for each 2m frame, and thus subtraction image B is obtained for each even frame. Subtraction image B is obtained for each (2m+1) frame (see "(or 2m+1)" in FIG. 6), and thus subtraction image B is obtained for each odd frame.

EMBODIMENT 3

Figure 7:
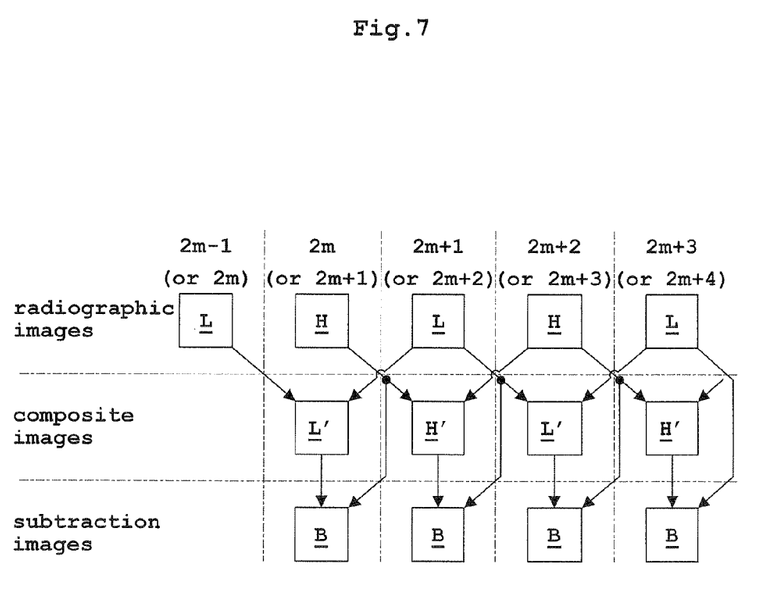
FIG. 7 is a schematic view showing data flows in Embodiment 3.

Next, Embodiment 3 of this invention will be described with reference to the drawings. FIG. 7 is a schematic view showing data flows in Embodiment 3.

As shown in FIG. 7, in this Embodiment 3, the composite image generating unit 9b generates a composite high-voltage image H' for every time of the same high voltage based on two high-voltage images H. The composite image generating unit 9b generates also a composite low-voltage image L' for every time of the same low voltage based on two low-voltage images L. In this Embodiment 3 in particular, as shown in FIG. 7, the composite image generating unit 9b generates a composite high-voltage image H' for (2m+1) frame based on the high-voltage image H of 2m frame and the high-voltage image H of (2m+2) frame. The composite image generating unit 9b generates also a composite low-voltage image L' for 2m frame based on the low-voltage image L of (2m−1) frame and the low-voltage image L of (2m+1) frame. As a specific example of generation, the composite high-voltage image H' for (2m+1) frame is generated by adding the high-voltage image H of 2m frame and the high-voltage image H of (2m+2) frame, and the composite low-voltage image L' for 2m frame is generated by adding the low-voltage image L of (2m−1) frame and the low-voltage image L of (2m+1) frame. The composite high-voltage images H' for (2m+1) frames and composite low-voltage images L' for 2m frames generated by the composite image generating unit 9b are written and stored in the composite image memory 11b, respectively.

The subtraction processing unit 9c carries out a subtraction process based on the low-voltage images L stored in the high- and low-voltage image memory 11a and the composite high-voltage images H'. The subtraction processing unit 9c carries out also a subtraction process based on the high-voltage images H stored in the high- and low-voltage image memory 11a and the composite low-voltage images L'. That is, the subtraction processing unit 9c carries out a subtraction process concerning the low-voltage images L and composite high-voltage images H', and the subtraction processing unit 9c carries out also a subtraction process concerning the high-voltage images H and composite low-voltage images L'. Subtraction images B processed by the subtraction processing unit 9c are written and stored in the subtraction image memory 11c, respectively.

To summarize the above, when X-rays corresponding to the low voltage value are emitted for the odd frames of (2m−1), and X-rays corresponding to the high voltage value are emitted for the even frames of 2m, in this Embodiment 3 the composite image generating unit 9b generates a composite low-voltage image L' for 2m frame based on low-voltage image L of (2m−1) frame and low-voltage image L of (2m+1) frame, and the composite image generating unit 9b generates also a composite high-voltage image H' for (2m+1) frame based on high-voltage image H of 2m frame and high-voltage image H of (2m+2) frame. The subtraction processing unit 9c carries out a subtraction process concerning the high-voltage image H of 2m frame and the composite low-voltage image L' of 2m frame, and the subtraction processing unit 9c carries out also a subtraction process concerning the low-voltage image L of (2m+1) frame and the composite high-voltage image H' of (2m+1) frame.

Conversely, when X-rays corresponding to the high voltage value are emitted for the odd frames of (2m−1), and X-rays corresponding to the low voltage value are emitted for the even frames of 2m, in this Embodiment 3 the composite image generating unit 9b generates a composite high-voltage image H' for 2m frame based on high-voltage image H of (2m−1) frame and high-voltage image H of (2m+1) frame (see "(or 2m+1)" in FIG. 7), and the composite image generating unit 9b generates also a composite low-voltage image L' for (2m+1) frame (see "(or 2m+1)" in FIG. 7) based on low-voltage image L of 2m frame (see "(or 2m)" in FIG. 7) and low-voltage image L of (2m+2) frame (see "(or 2m+2)" in FIG. 7). The subtraction processing unit 9c carries out a subtraction process concerning the low-voltage image L of 2m frame (see "(or 2m)" FIG. 7) and the composite high-voltage image H' of 2m frame, and the subtraction processing unit 9c carries out also a subtraction process concerning the high-voltage image H of (2m+1) frame (see "(or 2m+1)" in FIG. 7) and the composite low-voltage image L' of (2m+1) frame (see "(or 2m+1)" in FIG. 7).

According to the X-ray imaging apparatus in this Embodiment 3, as in Embodiments 1 and 2, the composite image generating unit 9b generates a composite high-voltage image for every time of the same high voltage based on a plurality of high-voltage images successively acquired by the high- and low-voltage image acquiring unit 9a, or generates a composite low-voltage image for every time of the same low voltage based on a plurality of low-voltage images successively acquired by the high- and low-voltage image acquiring unit 9a. The subtraction processing unit 9c acquires subtraction images by carrying out subtraction processes concerning the high-voltage images and the low-voltage images based on the composite high-voltage images or composite low-voltage images generated by the composite image generating unit 9b. Thus, a mistake by arithmetic processing is made inconspicuous without causing a dose shortage.

In this Embodiment 3, as shown in FIG. 7, the composite image generating unit 9b generates a composite high-voltage image H' for 2m frame based on the high-voltage image H of (2m−1) frame and the high-voltage image H of (2m+1) frame acquired by the high- and low-voltage image acquiring unit 9a, and the composite image generating unit 9b generates also a composite low-voltage image L' for (2m+1)

frame based on the low-voltage image L of 2m frame and the low-voltage image L of (2m+2) frame acquired by the high- and low-voltage image acquiring unit 9a. The subtraction processing unit 9c carries out a subtraction process concerning the low-voltage image L of 2m frame acquired by the high- and low-voltage image acquiring unit 9a and the composite high-voltage image H' of 2m frame generated by the composite image generating unit 9b, and the subtraction processing unit 9c carries out also a subtraction process concerning the high-voltage image H of (2m+1) frame acquired by the high- and low-voltage image acquiring unit 9a and the composite low-voltage image L' of (2m+1) frame generated by the composite image generating unit 9b.

Alternatively, the composite image generating unit 9b generates a composite low-voltage image L' for 2m frame based on the low-voltage image L of (2m−1) frame and the low-voltage image L of (2m+1) frame acquired by the high- and low-voltage image acquiring unit 9a, and the composite image generating unit 9b generates also a composite high-voltage image H' for (2m+1) frame based on the high-voltage image H of 2m frame and the high-voltage image H of (2m+2) frame acquired by the high- and low-voltage image acquiring unit 9a. The subtraction processing unit 9c carries out a subtraction process concerning the high-voltage image H of 2m frame acquired by the high- and low-voltage image acquiring unit 9a and the composite low-voltage image L' of 2m frame generated by the composite image generating unit 9b, and the subtraction processing unit 9c carries out also a subtraction process concerning the low-voltage image L of (2m+1) frame acquired by the high- and low-voltage image acquiring unit 9a and the composite high-voltage image H' of (2m+1) frame generated by the composite image generating unit 9b.

That is, when high-voltage image H is acquired in each odd frame and low-voltage image L is acquired in each even frame, a composite high-voltage image H' is generated based on high-voltage image H of (2m−1) frame and high-voltage image H of (2m+1) frame adjoining each other in time across the even frame of 2m frame, and this composite high-voltage image H' is regarded as the image of 2m frame interposed in between, while a composite low-voltage image L' is generated based on low-voltage image L of 2m frame and low-voltage image L of (2m+2) frame adjoining each other in time across the odd frame of (2m+1) frame, and this composite low-voltage image L' is regarded as the image of (2m+1) frame interposed in between. And a subtraction process is carried out on low-voltage image L and composite high-voltage image H', both being of 2m frame, while a subtraction process is carried out on high-voltage image H and composite low-voltage image L', both being of (2m+1) frame.

When low-voltage image L is acquired in each odd frame and high-voltage image H is acquired in each even frame, a composite low-voltage image L' is generated based on low-voltage image L of (2m−1) frame and low-voltage image L of (2m+1) frame adjoining each other in time across the even frame of 2m, and this composite low-voltage image L' is regarded as the image of 2m frame interposed in between, while a composite high-voltage image H' is generated based on high-voltage image H of 2m frame and high-voltage image H of (2m+2) frame adjoining each other in time across the odd frame of (2m+1), and this composite high-voltage image is regarded as the image of (2m+1) frame interposed in between. And a subtraction process is carried out on high-voltage image H and composite low-voltage image L', both being of 2m frame, while a subtraction process is carried out on low-voltage image L and composite high-voltage image H', both being of (2m+1) frame.

In this Embodiment 3, as shown in FIG. 7, subtraction image B is obtained for each of 2m frames and (2m+1) frames, and thus subtraction image B is obtained for each frame.

This invention is not limited to the foregoing embodiments, but may be modified as follows:

(1) In each of the foregoing embodiments, the X-ray imaging apparatus has been described as an example of radiographic apparatus. The invention may be applied to a radiographic apparatus, such as an ECT (Emission Computed Tomography) apparatus represented by a PET (Positron Emission Tomography) apparatus or a SPECT (Single Photon Emission CT) apparatus, which carries out radiation image pickup by detecting radiation other than X-rays (gamma rays in the case of the PET apparatus) and obtaining radiographic images based on the detected radiation.

(2) In each of the foregoing embodiments, the X-ray imaging apparatus as shown in FIG. 1 has been described by way of example. This invention may be applied to an X-ray imaging apparatus mounted on a C-shaped arm, for example. This invention may be applied also to an X-ray CT apparatus.

(3) In each of the foregoing embodiments, the flat panel X-ray detector has been described as an example of radiation detecting device. There is no limitation as long as the device is an X-ray detecting device used generally, such as an image intensifier (I.I). As in the case of being applied to an ECT apparatus, as in modification (1) above, there is no limitation as long as it is a radiation detecting device used generally.

(4) In each of the foregoing embodiments, the high- and low-voltage image acquiring unit 9a acts as the high-voltage image acquiring device and low-voltage image acquiring device in this invention. However, separate image acquiring units may carry out independently the functions of the high-voltage image acquiring device and low-voltage image acquiring device, respectively.

(5) In each of the foregoing embodiments, as an example of composite (high-voltage/low-voltage) image generation, a composite high-voltage image is generated by adding a plurality of high-voltage images, or a composite low-voltage image is generated by adding a plurality of low-voltage images. However, the composite (high-voltage/low-voltage) image generation is not limited thereto. For example, a composite high-voltage image may be generated by additive average (i.e. arithmetic average) in which a plurality of high-voltage images are added and the result is divided by the number of high-voltage images added, or a composite low-voltage image may be generated by additive average (arithmetic average) in which a plurality of low-voltage images are added and the result is divided by the number of low-voltage images added.

Specifically, a composite high-voltage image for 2m frame is generated by additive average in which a high-voltage image of (2m−1) frame and a high-voltage image of (2m+1) frame are added, and the result is divided by 2 which is the number of high-voltage images added. Or a composite high-voltage image for (2m+1) frame is generated by additive average in which a high-voltage image of 2m frame and a high-voltage image of (2m+2) frame are added, and the result is divided by 2 which is the number of high-voltage images added.

Or a composite low-voltage image for 2m frame is generated by additive average in which a low-voltage image of (2m−1) frame and a low-voltage image of (2m+1) frame are added, and the result is divided by 2 which is the number of high-voltage images added. Or a composite low-voltage image for (2m+1) frame is generated by additive average in which a low-voltage image of 2m frame and a low-voltage image of (2m+2) frame acquired by the low-voltage image acquiring device are added, and the result is divided by 2 which is the number of low-voltage images added.

A composite (high-voltage/low-voltage) image may be generated by techniques other than the above addition and additive average (arithmetic average). For example, a composite (high-voltage/low-voltage) image may be generated by weighting addition. It is also possible to divide a high-voltage/low-voltage image into minute parts, calculate amounts of motion of the divided minute parts, and apply a technique of image morphing.

(6) In each of the foregoing embodiments, a composite high-voltage/low-voltage image is generated based on a high-voltage/low-voltage image of (2m−1) frame and a high-voltage/low-voltage image of (2m+1) frame adjoining each other in time across the even frame of 2m frame, or a composite high-voltage/low-voltage image is generated based on a high-voltage/low-voltage image of 2m frame and a high-voltage/low-voltage image of (2m+2) frame adjoining each other in time across the odd frame of (2m+1) frame. However, it is not absolutely necessary to generate a composite high-voltage/low-voltage image based on high-voltage/low-voltage images of two frames adjoining each other in time across an even or odd frame. A composite high-voltage image for every time of the same high voltage may be generated based on a plurality of, three or more, high-voltage images, or a composite low-voltage image for every time of the same low voltage may be generated based on a plurality of, three or more, low-voltage images. For example, composite high-voltage/low-voltage images may be generated by spline interpolation using high-voltage/low-voltage images of four frames adjoining each other in time across even or odd frames.

The invention claimed is:

1. A radiographic apparatus having a radiation emitting device for emitting radiation toward a patient, and a radiation detecting device for detecting radiation transmitted through the patient, to carry out radiation image pickup by obtaining radiographic images based on the detected radiation, the radiation emitting device being constructed to emit, as switched back and forth, radiation corresponding to a first voltage value and radiation corresponding to a second voltage value lower than the first voltage value, the radiation detecting device being constructed to detect alternately the radiation corresponding to the first voltage value and the radiation corresponding to the second voltage value, and to output alternately radiation detection signals corresponding to the first voltage value and radiation detection signals corresponding to the second voltage value, the apparatus comprising a high-voltage image acquiring device for acquiring high-voltage images based on the radiation detection signals corresponding to the first voltage value detected, a low-voltage image acquiring device for acquiring low-voltage images based on the radiation detection signals corresponding to the second voltage value detected, a composite image generating device for generating a composite high-voltage image for every time of the same first voltage as a frame in time between a plurality of frames to be composite, or generating a composite low-voltage image for every time of the same second voltage as a frame in time between a plurality of frames to be composite, and a subtraction processing device for carrying out a subtraction process concerning the high-voltage images and the low-voltage images in the frames same in time, thereby to acquire subtraction images.

2. The radiographic apparatus according to claim 1, wherein, when m is a natural number, (A) the composite image generating device is arranged to generate a composite low-voltage image for 2m frame based on a low-voltage image of (2m−1) frame and a low-voltage image of (2m+1) frame acquired by the low-voltage image acquiring device, and the subtraction processing device is arranged to carry out a subtraction process concerning a high-voltage image of 2m frame acquired by the high-voltage image acquiring device and the composite low-voltage image of 2m frame generated by the composite image generating device, or (B) the composite image generating device is arranged to generate a composite low-voltage image for (2m+1) frame based on a low-voltage image of 2m frame and a low-voltage image of (2m+2) frame acquired by the low-voltage image acquiring device, and the subtraction processing device is arranged to carry out a subtraction process concerning a high-voltage image of (2m+1) frame acquired by the high-voltage image acquiring device and the composite low-voltage image of (2m+1) frame generated by the composite image generating device.

3. The radiographic apparatus according to claim 1, wherein, when m is a natural number, (C) the composite image generating device is arranged to generate a composite high-voltage image for 2m frame based on a high-voltage image of (2m−1) frame and a high-voltage image of (2m+1) frame acquired by the high-voltage image acquiring device, and the subtraction processing device is arranged to carry out a subtraction process concerning a low-voltage image of 2m frame acquired by the low-voltage image acquiring device and the composite high-voltage image of 2m frame generated by the composite image generating device, or (D) the composite image generating device is arranged to generate a composite high-voltage image for (2m+1) frame based on a high-voltage image of 2m frame and a high-voltage image of (2m+2) frame acquired by the high-voltage image acquiring device, and the subtraction processing device is arranged to carry out a subtraction process concerning a low-voltage image of (2m+1) frame acquired by the low-voltage image acquiring device and the composite high-voltage image of (2m+1) frame generated by the composite image generating device.

4. The radiographic apparatus according to claim 1, wherein, when m is a natural number, (E) the composite image generating device is arranged to generate a composite high-voltage image for 2m frame based on a high-voltage image of (2m−1) frame and a high-voltage image of (2m+1) frame acquired by the high-voltage image acquiring device, while the composite image generating device is arranged to generate a composite low-voltage image for (2m+1) frame based on a low-voltage image of 2m frame and a low-voltage image of (2m+2) frame acquired by the low-voltage image acquiring device, and the subtraction processing device is arranged to carry out a subtraction process concerning a low-voltage image of 2m frame acquired by the low-voltage image acquiring device and the composite high-voltage image of 2m frame generated by the composite image generating device, while the subtraction processing device is arranged to carry out a subtraction process concerning a high-voltage image of (2m+1) frame acquired by the high-voltage image acquiring device and the composite low-voltage image of (2m+1) frame generated by the composite image generating device, or (F) the composite image generating device is arranged to generate a composite low-voltage image for 2m frame based on a low-voltage image of (2m−1) frame and a low-voltage image of (2m+1) frame acquired by the low-voltage image acquiring device, while the composite image generating device is arranged to generate a composite high-voltage image for (2m+1) frame based on a high-voltage image of 2m frame and a high-voltage image of (2m+2) frame acquired by the high-voltage image acquiring device, and the subtraction processing device is arranged to carry out a subtraction process concerning a high-voltage image of 2m frame acquired by the high-voltage image acquiring device and the composite low-voltage image of 2m frame generated by the composite image generating device, while the subtraction processing device is arranged to carry out a subtraction process concerning a low-voltage image of (2m+1) frame acquired by the low-voltage image acquiring device and the composite high-voltage image of (2m+1) frame generated by the composite image generating device.

5. The radiographic apparatus according to claim 1, wherein the composite image generating device is arranged to generate the composite high-voltage image by adding a plurality of high-voltage images successively acquired by the high-voltage image acquiring device, or the composite image generating device is arranged to generate the composite low-voltage image by adding a plurality of low-voltage images successively acquired by the low-voltage image acquiring device.

6. The radiographic apparatus according to claim 5, wherein, when m is a natural number, the composite image generating device is arranged to generate the composite high-voltage image for 2m frame by adding a high-voltage image of (2m−1) frame and a high-voltage image of (2m+1) frame acquired by the high-voltage image acquiring device, or the composite image generating device is arranged to generate the composite high-voltage image for (2m+1) frame by adding a high-voltage image of 2m frame and a high-voltage image of (2m+2) frame acquired by the high-voltage image acquiring device.

7. The radiographic apparatus according to claim 5, wherein, when m is a natural number, the composite image generating device is arranged to generate the composite low-voltage image for 2m frame by adding a low-voltage image of (2m−1) frame and a low-voltage image of (2m+1) frame acquired by the low-voltage image acquiring device, or the composite image generating device is arranged to generate the composite low-voltage image for (2m+1) frame by adding a low-voltage image of 2m frame and a low-voltage image of (2m+2) frame acquired by the low-voltage image acquiring device.

8. The radiographic apparatus according to claim 1, wherein the composite image generating device is arranged to generate the composite high-voltage image by additive average in which a plurality of high-voltage images successively acquired by the high-voltage image acquiring device are added and the result is divided by the number of high-voltage images added, or to generate the composite low-voltage image by additive average in which a plurality of low-voltage images successively acquired by the low-voltage image acquiring device are added and the result is divided by the number of low-voltage images added.

9. The radiographic apparatus according to claim 8, wherein, when m is a natural number, the composite image generating device is arranged to generate the composite high-voltage image for 2m frame by additive average in which a high-voltage image of (2m−1) frame and a high-voltage image of (2m+1) frame acquired by the high-voltage image acquiring device are added, and the result is divided by 2 which is the number of high-voltage images added, or the composite image generating device is arranged to generate the composite high-voltage image for (2m+1) frame by additive average in which a high-voltage image of 2m frame and a high-voltage image of (2m+2) frame acquired by the high-voltage image acquiring device are added, and the result is divided by 2 which is the number of high-voltage images added.

10. The radiographic apparatus according to claim 8, wherein, when m is a natural number, the composite image generating device is arranged to generate the composite low-voltage image for 2m frame by additive average in which a low-voltage image of (2m−1) frame and a low-voltage image of (2m+1) frame acquired by the low-voltage image acquiring device are added, and the result is divided by 2 which is the number of low-voltage images added, or the composite image generating device is arranged to generate the composite low-voltage image for (2m+1) frame by additive average in which a low-voltage image of 2m frame and a low-voltage image of (2m+2) frame acquired by the low-voltage image acquiring device are added, and the result is divided by 2 which is the number of low-voltage images added.

\* \* \* \* \*